United States Patent
Kim et al.

(10) Patent No.: US 10,835,564 B2
(45) Date of Patent: Nov. 17, 2020

(54) COMPOSITION FOR PREVENTING AND TREATING PREMATURE OVARIAN FAILURE, CONTAINING EVODIA RUTAECARPA BENTHAM EXTRACT HAVING PROTECTIVE ACTIVITY AGAINST OVOTOXICITY

(71) Applicant: DONGGUK UNIVERSITY GYEONGJU CAMPUS INDUSTRY-ACADEMY COOPERATION FOUNDATION, Gyeongju-si (KR)

(72) Inventors: Dongil Kim, Goyang-si (KR); Ju-Hee Lee, Goyang-si (KR); Heejung Kim, Seoul (KR)

(73) Assignee: DONGGUK UNIVERSITY GYEONGJU CAMPUS INDUSTRY-ACADEMY COOPERATION FOUNDATION, Gyeongju-si (KR)

( * ) Notice: Subject to any disclaimer, the term of this patent is extended or adjusted under 35 U.S.C. 154(b) by 183 days.

(21) Appl. No.: 16/305,129

(22) PCT Filed: Oct. 10, 2016

(86) PCT No.: PCT/KR2016/011302
§ 371 (c)(1),
(2) Date: Nov. 28, 2018

(87) PCT Pub. No.: WO2017/095011
PCT Pub. Date: Jun. 8, 2017

(65) Prior Publication Data
US 2019/0183957 A1    Jun. 20, 2019

(30) Foreign Application Priority Data

Dec. 2, 2015  (KR) .......... 10-2015-0170364
Oct. 7, 2016  (KR) .......... 10-2016-0129640

(51) Int. Cl.
*A61K 36/754* (2006.01)
*A61P 15/08* (2006.01)
*A61P 39/06* (2006.01)
*A23L 2/00* (2006.01)

(52) U.S. Cl.
CPC .............. *A61K 36/754* (2013.01); *A23L 2/00* (2013.01); *A61P 15/08* (2018.01); *A61P 39/06* (2018.01)

(58) Field of Classification Search
None
See application file for complete search history.

(56) References Cited

FOREIGN PATENT DOCUMENTS

| | | |
|---|---|---|
| JP | 2005-298450 A | 10/2005 |
| JP | 2012-025717 A | 2/2012 |
| KR | 10-1999-0011833 A | 2/1999 |
| KR | 10-2002-0037292 A | 5/2002 |
| KR | 10-2009-0031297 A | 3/2009 |
| KR | 10-2014-0108942 A | 9/2014 |

OTHER PUBLICATIONS

English translation of JP 2005-298450 A—Oct. 2005.*
PCT International Search Report and Written Opinion dated Jan. 11, 2017 in corrersponding Application No. PCT/KR2016/011302, 9 pages.
Zhong et al., Scientific Report 5 published on Nov. 10, 2015.
Rebhun et al., Fitoterapia 101 (2014), pp. 57-63.

* cited by examiner

*Primary Examiner* — Susan Hoffman
(74) *Attorney, Agent, or Firm* — Dilworth IP, LLC

(57) ABSTRACT

The present invention relates to a pharmaceutical composition for preventing or treating ovotoxicity, and more specifically, to a pharmaceutical composition for preventing or treating ovotoxicity, containing an *Evodia rutaecarpa* Bentham extract. According to the present invention, the *Evodia rutaecarpa* Bentham extract concentration-dependently increases DPPH free radical scavenging activity so as to have excellent antioxidant activity, inhibits apoptosis of ovarian cells, and activates a PI3K/Akt signaling pathway so as to have a significant protective effect against ovotoxicity to be caused by 4-vinylcyclohexene diepoxide (VCD), thereby being usable as a medicine and a health functional food, which are useful for alleviating, preventing, inhibiting or treating ovotoxicity, premature ovarian failure and the like. Therefore, subfertility treatment or prevention, premature ovarian failure, a menopausal disorder in the premenopausal period, and the like can be considered application examples related thereto.

4 Claims, 16 Drawing Sheets

COMPOSITION FOR PREVENTING AND TREATING PREMATURE OVARIAN FAILURE, CONTAINING EVODIA RUTAECARPA BENTHAM EXTRACT HAVING PROTECTIVE ACTIVITY AGAINST OVOTOXICITY

TECHNICAL FIELD

The present invention relates to a composition for preventing or treating ovotoxicity, and more specifically, to a composition for preventing or treating ovotoxicity, containing an *Evodia rutaecarpa* Bentham extract, or a composition for preventing or treating premature ovarian failure, containing the same.

BACKGROUND

The reproductive aging of sex may be caused by not only natural aging, but also by various environmental factors. An ovarian dysfunction occurring before the age of 40 due to the reproductive aging refers to premature ovarian failure.

Premature ovarian failure is a clinical condition which occurs while ovarian follicles in the ovary disappear or do not respond due to various factors. Premature ovarian failure occurs in about 1% of women before the age of 40, and it is known that 10 to 28% of primary amenorrhea and 4 to 18% of secondary amenorrhea occur due to premature ovarian failure. Unlike menopause where the ovary completely ceases to function, pregnancy may be possible in 5 to 10% of premature ovarian failure, but the prognosis of premature ovarian failure cannot be inferred. Such premature ovarian failure may be caused by genetic factors and ovarian damage due to autoimmunity, and examples of the causes of premature ovarian failure include iatrogenic causes such as anti-cancer treatment, radiation treatment, and ovarian surgery, or virus infection, or environmental factors such as drugs and smoking, but there are many cases where it is difficult to explain the occurrence mechanism and causes of premature ovarian failure in most patients. For such premature ovarian failure, early menopause may cause patients to complain of more serious menopause-related symptoms earlier and more obviously than natural menopausal women. Early menopause may become a major antecedent cause of not only impairment of emotional well-being and sexual self, but also deterioration in health-related quality of life such as cardiovascular diseases and osteoporosis, in consideration of life expectancy after menopause.

In the Oriental traditional medicine, symptoms related to premature ovarian failure are expressed as "not yet old, menstrual water cut-off", but can be found widely within the range of menopause. The <Suwen> "Shanggutlanzhenlun" translated into "The treatise on the Natural Truth in Ancient Times" in the book Suwen mentioned "Qīqī rèn mài xū, tài chōngmài shuāi shǎo tiānguǐ jié, dìdào bùtōng, gù xíng huài ér wú zǐ yě", meaning that women generally experience menopause at the age of 49, which is caused by a natural aging process, and conversely, the "Fu Qing Zhu Andrology and Gynecology" defined menopause caused by premature ovarian failure as a morbid status in which menstruation is terminated before women reach the menopause by mentioning 'N[ $ ]$ ¨$$[ $ ]$ ¨Ahüzǐ qīqī tiān guǐ jué wèi jǐ jǐ nián ér xiān jīng duàn zhě.

Meanwhile, 4-vinylcyclohexene diepoxide (VCD) is a material that has been typically used to prepare rubber tires, polyesters and plastics. However, the VCD has attracted attention as a chemical material of environmental factors related to reproductive aging. The VCD selectively causes destruction of ovarian small pre-antral (primordial and primary) follicles by accelerating the natural apoptosis process. Further, the VCD is a material that selectively destroys the primordial follicle in a white paper model, and directly interacts with the oocyte-associated c-kit receptor to inhibit the autophosphorylation thereof, thereby impairing oocyte viability. In this process, it is known that while a distribution problem of a kit occurs, the activity of a PI3K protein in the downstream and Akt, which is the PI3K family, are also affected.

Therefore, various studies have been conducted to develop therapeutic agent materials for treating the ovotoxcity, more specifically, VCD-induced ovotoxicity and premature ovarian failure through the same, and in particular, studies on herbal medicines that are harmless to the human body and thus can be taken safely for a long time have been actively conducted (Japanese Patent Application Laid-Open No. JP2005-298450), but are still incomplete.

DETAILED DESCRIPTION OF THE INVENTION

Technical Problem

The present invention has been devised to solve the problems in the related art as described above, and as a result of intensive studies to discover a herbal medicine extract material effective for premature ovarian failure, the present inventors confirmed that an *Evodia rutaecarpa* Bentham extract has a significant protective effect against ovotoxicity to be caused by 4-vinylcyclohexene diepoxide (VCD), and accordingly, the *Evodia rutaecarpa* Bentham extract has effects on the prevention or treatment of premature ovarian failure, thereby completing the present invention based on the confirmation.

Accordingly, an object of the present invention is to provide a pharmaceutical composition for preventing or treating ovotoxicity, containing an *Evodia rutaecarpa* Bentham extract as an effective ingredient.

Another object of the present invention is to provide a pharmaceutical composition or a health functional food composition for preventing, alleviating, or treating premature ovarian failure, containing an *Evodia rutaecarpa* Bentham extract as an effective ingredient.

However, a technical problem to be achieved by the present invention is not limited to the aforementioned problem, and the other problems that are not mentioned will be clearly understood by a person skilled in the art from the following description.

Technical Solution

In order to achieve the objects, the present invention provides a pharmaceutical composition for preventing or treating ovotoxicity, containing an *Evodia rutaecarpa* Bentham extract as an effective ingredient.

As an exemplary embodiment of the present invention, the ovotoxicity may be caused by 4-vinylcyclohexene diepoxide (VCD).

As another exemplary embodiment of the present invention, the *Evodia rutaecarpa* Bentham extract may inhibit apoptosis of ovarian cells.

As still another exemplary embodiment of the present invention, the *Evodia rutaecarpa* Bentham extract may activate a PI3K/Akt signaling pathway.

Further, the present invention provides a pharmaceutical composition for preventing or treating premature ovarian failure, containing an *Evodia rutaecarpa* Bentham extract as an effective ingredient.

In addition, the present invention provides a health functional food composition for alleviating premature ovarian failure, containing an *Evodia rutaecarpa* Bentham extract as an effective ingredient.

Furthermore, the present invention provides a method for preventing or treating premature ovarian failure, the method including: administering an *Evodia rutaecarpa* Bentham extract to an individual.

Further, the present invention provides a use of an *Evodia rutaecarpa* Bentham extract for preventing or treating premature ovarian failure.

Effects of the Invention

According to the present invention, the *Evodia rutaecarpa* Bentham extract concentration-dependently increases DPPH free radical scavenging activity so as to have excellent antioxidant activity, inhibits apoptosis of ovarian cells, and activates a PI3K/Akt signaling pathway so as to have a significant protective effect against ovotoxicity to be caused by 4-vinylcyclohexene diepoxide (VCD), thereby being usable as a medicine and a health functional food, which are useful for alleviating, preventing, inhibiting or treating ovotoxicity, premature ovarian failure, and the like. Therefore, infertility or subfertility treatment or prevention, premature ovarian failure, a menopausal disorder in the premenopausal period, and the like can be considered application examples related thereto.

BEST MODE

Figure 1:
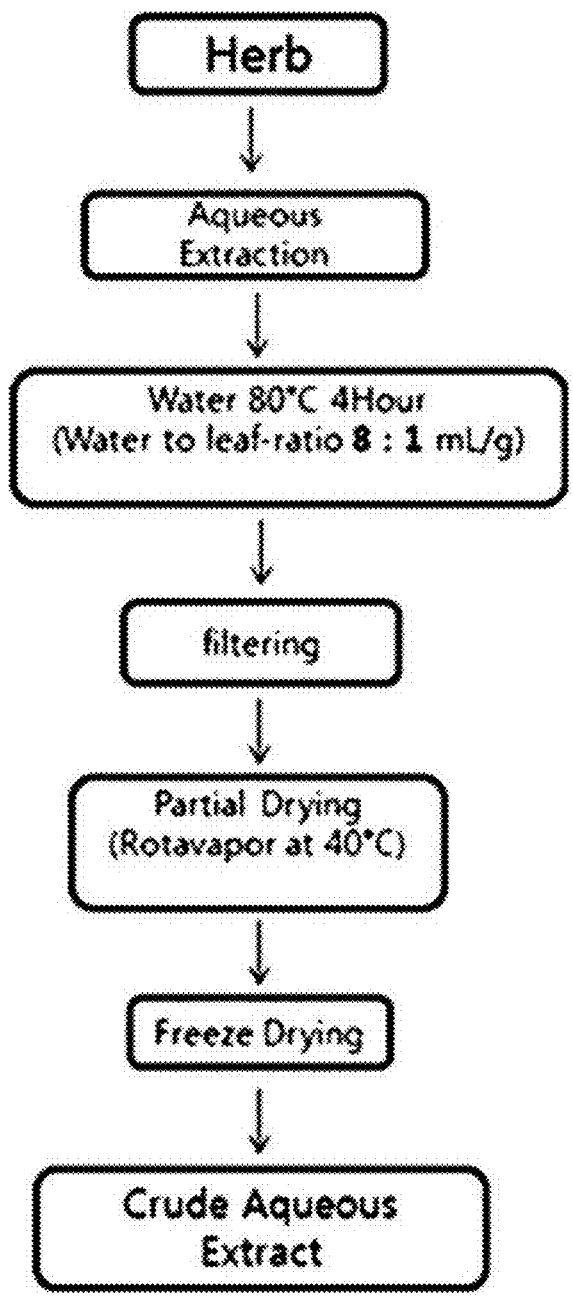
FIG. 1 is a flowchart schematically illustrating a process of preparing an *Evodia rutaecarpa* Bentham extract.

The present invention provides a pharmaceutical composition for preventing or treating ovotoxicity, containing an *Evodia rutaecarpa* Bentham extract as an effective ingredient.

In the present invention, "ovotoxicity" means that the ovary is damaged by a chemical cause, and the damage includes all of those in which the ovarian function is lost or ovarian cells undergo apoptosis.

The *Evodia rutaecarpa* Bentham extract, which is an effective ingredient in the composition of the present invention, may be obtained by a typical extraction method, and those commercially available may be purchased and used. Examples of the typical extraction method include hot water extraction, cold immersion extraction, reflux extraction, ultrasonic extraction, and the like, but are not limited thereto.

In the present invention, the *Evodia rutaecarpa* Bentham extract may be obtained by the following method. First, *Evodia rutaecarpa* Bentham is cleanly washed with water and dried, and then mixed and ground. The ground mixture is reflux extracted with water, a $C_1$ to $C_4$ alcohol, or a mixed solvent of water and a $C_1$ to $C_4$ alcohol at 50 to 100° C. for 2 to 5 hours, preferably 4 hours. In this case, the volume of the solvent is set to 1 to 10 times, preferably 5 to 8 times the weight of the ground *Evodia rutaecarpa* Bentham. Thereafter, the extracted liquid is filtered, the filtrate is concentrated, and then an *Evodia rutaecarpa* Bentham extract in the form of a powder is obtained by freeze-drying the concentrated liquid.

In the present invention, it is known that 4-vinylcyclohexene diepoxide (VCD) selectively causes destruction of ovarian small pre-antral (primordial and primary) follicles by accelerating the natural apoptosis process, and the present inventors observed the effects of the *Evodia rutaecarpa* Bentham extract in ovotoxicity caused by the VCD.

In an Example of the present invention, as a result of confirming the protective efficacy of an *Evodia rutaecarpa* Bentham extract from ovotoxicity by VCD by pre-treating CHO-K1 cells which are hamster ovary-derived chemotactic cells with the *Evodia rutaecarpa* Bentham extract, and then treating the cells with VCD, it was confirmed that the *Evodia rutaecarpa* Bentham extract has a remarkably excellent protective effect as compared to medicine extracts used to treat infertility in the related art (see Example 4), and also inhibits apoptosis caused by VCD (see Example 7).

In another Example of the present invention, as a result of confirming the activation of a PI3K/Akt signaling pathway in order to examine the mechanism of the protective efficacy of the *Evodia rutaecarpa* Bentham extract against ovotoxicity, it was confirmed that the *Evodia rutaecarpa* Bentham extract increases the activity of PI3K/Akt (see Example 8).

Accordingly, the *Evodia rutaecarpa* Bentham extract according to the present invention exhibits an excellent protective effect against germ cell toxicity caused by VCD which is a representative ovarian toxic material, thereby being usable as a medicine and a health functional food, which are useful for alleviating, preventing, inhibiting or treating premature ovarian failure, infertility, subfertility, a menopausal disorder in the premenopausal period, and the like.

Thus, as another aspect of the present invention, the present invention provides a pharmaceutical composition for preventing or treating premature ovarian failure, containing an *Evodia rutaecarpa* Bentham extract as an effective ingredient.

The term "prevention" used in the present invention means all actions that suppress premature ovarian failure or delay the onset of the premature ovarian failure by administering the pharmaceutical composition according to the present invention.

The term "treatment" used in the present invention means all actions that ameliorate or beneficially change symptoms caused by premature ovarian failure by administering the pharmaceutical composition according to the present invention.

"Premature ovarian failure" as a disease to be targeted in the present invention means that the function of the ovary has stopped due to various factors in women who showed normal development before the age of 40, and also includes the depletion or dysfunction of ovarian follicles.

The pharmaceutical composition of the present invention may further contain publicly-known one or more effective ingredients having an effect of treating ovotoxicity or premature ovarian failure together with the *Evodia rutaecarpa* Bentham extract.

The pharmaceutical composition of the present invention may further include an appropriate carrier, an appropriate excipient, and an appropriate diluent, which are typically used to prepare a pharmaceutical composition. Further, the pharmaceutical composition may be used by being formulated in the form of an oral formulation such as a powder, a granule, a pill, a capsule, a suspension, an emulsion, a syrup, and an aerosol, an external preparation, a suppository, and a sterile injection solution, according to a typical method.

Examples of the carrier, the excipient, and the diluent, which may be included in the composition, include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, and the like. When the composition is prepared, the composition is prepared by using a diluent or excipient, such as a filler, an extender, a binder, a wetting agent, a disintegrant, and a surfactant, commonly used.

The pharmaceutical composition of the present invention may be orally administered or may be parenterally administered (for example, applied intravenously, subcutaneously, intraperitoneally, or locally), and the administration dose may vary depending on a patient's condition and body weight, severity of disease, drug form, and administration route and period according to the target method, but the administration dose may be properly selected by the person skilled in the art.

The pharmaceutical composition of the present invention is administered in a pharmaceutically effective amount. In the present invention, "pharmaceutically effective amount" means an amount sufficient to treat diseases at a reasonable benefit/risk ratio applicable to medical treatment, and an effective dosage level may be determined according to factors including type of diseases of patients, the severity of disease, the activity of drugs, sensitivity to drugs, administration time, administration route, excretion rate, treatment period, and simultaneously used drugs, and factors well known in other medical fields. The pharmaceutical composition of the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount can be easily determined by the person skilled in the art.

Specifically, an effective amount of the pharmaceutical composition of the present invention may vary according to the age, sex, condition, and body weight of a patient, the absorption of the active ingredients in the body, inert rate and excretion rate, disease type, and the drugs used in combination, and in general, 0.0001 to 150 mg, preferably 0.001 to 100 mg of the pharmaceutical composition of the present invention per 1 kg of a body weight may be administered daily or every other day or may be dividedly administered once to three times a day. However, since the dosage may be increased or decreased depending on the administration route, the severity of obesity, the gender, the body weight, the age, and the like, the dosage is not intended to limit the scope of the present invention by any method.

In addition, as still another aspect of the present invention, the present invention provides a health functional food composition for alleviating premature ovarian failure, containing an *Evodia rutaecarpa* Bentham extract as an effective ingredient.

The term "alleviation" used in the present invention refers to all actions of at least reducing a parameter associated with a condition to be treated, for example, the degree of symptom.

The composition of the present invention may be added to a health functional food for the purpose of preventing or alleviating premature ovarian failure. When the *Evodia rutaecarpa* Bentham extract of the present invention is used as a food additive, the *Evodia rutaecarpa* Bentham extract may be added as it is or used with another food or other food ingredients, and may be appropriately used according to a typical method. The amount of effective ingredient mixed may be suitably determined according to the purpose of use (prevention, health or therapeutic treatment) In general, when a food or beverage is prepared, the *Evodia rutaecarpa* Bentham extract of the present invention is added in an amount of 15 wt % or less, preferably 10 wt % or less based on the raw material. However, in the case of long-term intake for the purpose of health and hygiene, or for the purpose of controlling health, the amount may be equal to or less than the above range, and the effective ingredient may be used in an amount equal to or more than the above range due to no problem in terms of safety.

The type of food is not particularly limited. Examples of food to which the material may be added include meats, sausage, bread, chocolate, candies, snacks, confectioneries, pizza, instant noodles, other noodles, gums, dairy products including ice creams, various soups, beverage, tea, drinks, alcoholic beverages, vitamin complexes, and the like, and include all the health functional foods in a typical sense.

The health beverage composition of the present invention may contain various flavors or natural carbohydrates, and the like as an additional ingredient, as in a typical beverage. The above-described natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As a sweetener, it is possible to use a natural sweetener such as thaumatin and stevia extract, a synthetic sweetener such as saccharin and aspartame, and the like. The proportion of the natural carbohydrate is generally about 0.01 to 0.20 g, and preferably about 0.04 to 0.10 g per 100 ml of the composition of the present invention.

In addition to the aforementioned ingredients, the composition of the present invention may contain various nutrients, vitamins, electrolytes, flavors, colorants, pectic acids and salts thereof, alginic acid and salts thereof, organic acids, protective colloid thickeners, pH adjusters, stabilizers, preservatives, glycerin, alcohols, carbonating agents used in carbonated drinks, and the like. In addition, the composition of the present invention may contain flesh for preparing natural fruit juice, fruit juice drinks, and vegetable drinks. These ingredients may be used either alone or in combinations thereof. The proportion of these additives is not significantly important, but is generally selected within a range of 0.01 to 0.20 part by weight per 100 parts by weight of the composition of the present invention.

In addition, as yet another aspect of the present invention, the present invention provides a method for preventing or treating premature ovarian failure, infertility, subfertility, or a menopausal disorder in the premenopausal period, the method including administering an *Evodia rutaecarpa* Bentham extract to an individual. The individual is a mammal including a human or non-human, and the non-human mammal includes a mouse, a rat, a dog, a cat, a horse, a cow, a sheep, a goat, a pig, a rabbit, and the like, but is not limited thereto.

Hereinafter, preferred Examples for helping the understanding of the present invention will be suggested. However, the following Examples are provided only to more easily understand the present invention, and the contents of the present invention are not limited by the following Examples.

EXAMPLES

Example 1. Experimental Preparation and Experimental Method 1-1. Preparation of Medicine Extract

*Evodia rutaecarpa* Bentham, and Cuscutae Semen, Artemisiae Argyi Folium, Dioscoreae Rhizoma, Aucklandiae Radix, and Ulmi cortex, which had been used to treat infertility, were used in the experiment, and as the medicines, medicines obtained by purchasing, sorting, and carefully selecting oriental herbal medicines from Omni-herb Co., Ltd., were used. 800 ml of distilled water was added to 100 g of each of *Evodia rutaecarpa* Bentham, Cuscutae Semen, Artemisiae Argyi Folium, Dioscoreae Rhizoma, Aucklandiae Radix, and Ulmi cortex, and each of the resulting products was heated and reflux extracted for 4 hours. After the extract was cooled to room temperature and filtered twice with a 8 μm pore size filter paper, the filtered solution was concentrated under reduced pressure and freeze-dried, and the freeze-dried product was ground into powder to obtain the extract of each medicine as in the following Table 1 (see FIG. 1).

TABLE 1

| Herbal name | *Evodia rutaecarpa* Bentham | *Cuscutae Semen* | *Artemisiae Argyi Folium* | *Dioscoreae Rhizoma* | *Aucklandiae Radix* | *Ulmi cortex* |
|---|---|---|---|---|---|---|
| Latin name | *Evodiae Fructus* (EF) | *Cuscutae Semen* (CS) | *Artemisiae Argyi Folium* (AAF) | *Dioscoreae Rhizoma* (DR) | *Aucklandiae Radix* (AR) | *Ulmi cortex* (UC) |
| Yield (g) | 16.5/100 | 15.7/100 | 8.5/60 | 8.4/100 | 53.4/100 | 10.9/100 |
| Yield (%) | 16.5 | 15.7 | 14.2 | 8.4 | 53.4 | 10.9 |

1-2. Measurement of DPPH Radical Scavenging Activity

The scavenging activity against DPPH radicals was measured by a method publicly-known in the related art. More specifically, 1 ml of a 1 M DPPH solution and 450 μl of a 50 mM Tris-HCl buffer (pH 7.4) were first added to and mixed with 50 μl of a sample. The mixture was allowed to react at room temperature for 30 minutes, and then the absorbance was measured at a wavelength of 517 nm by using a microplate reader (VersaMax, Molecular Devices, USA). The scavenging activity of DPPH radicals was expressed as a concentration ($IC_{50}$) showing 50% scavenging ability.

1-3. Measurement of Superoxide Anion Scavenging Activity

As another index of the antioxidant activity, the scavenging activity against superoxide anions, which are one of the representative active oxygen species, was measured by using an NBT reduction method. More specifically, 10 μl of 30 mM EDTA (pH 7.4), 1 μl of 30 mM hypoxanthine, and 200 μl of 1.42 mM NBT were added to 30 μl of a sample, and after the resulting mixture was allowed to react at room temperature for 3 minutes, 10 μl of 1 U/ml xanthine oxidase was added thereto, and the total volume was adjusted to 300 μl by using a 50 mM phosphate buffer (pH 7.4). After the reaction solution was cultured at room temperature for 20 minutes, the absorbance was measured at a wavelength of 560 nm, and the result was expressed in terms of an NBT reduction $IC_{50}$ value by superoxide radicals.

1-4. MTT Assay

The cell viability was analyzed by a 3-(4,5-dimethylthiazol)-2,5-diphenyltetrazolium bromide (MTT) assay method. After CHO-K1 cells at $2\times10^4$ cells/well were cultured in a 48-well plate and then serum starved for 4 hours, VCD was treated at various concentrations or the respective medicines were pre-treated at 100 μg/ml, VCD (1.5 mM) was sequentially treated, and the cells were cultured under the conditions of 37° C. and 5% $CO_2$ for 24 hours. After 30 μl of an MTT solution (2 mg/ml) per well was added thereto and the resulting mixture was allowed to react in an incubator at 37° C. and 5% $CO_2$ for 3 hours, the MTT solution and the culture solution were completely removed, and then formazan crystallites formed in the cells were dissolved by using 150 μl of dimethyl sulfoxide (DMSO, Sigma-Aldrich, USA), and the absorbance thereof was measured at 595 nm by using an ELISA plate reader (DYNEX, Opsys MR, USA). The cell viability for the control was expressed as a percentage.

1-5. Western Blot

For extraction of proteins for electrophoresis, cells were washed three times with PBS, and then an RIPA buffer was added thereto, the resulting mixture was allowed to react at 4° C. for 30 minutes, and the supernatant was collected by centrifuging the resulting product at 12,000×g for 30 minutes. After the same amount of protein was separated by sodium dodecyl sulfatepolyacrylamide gel electrophoresis (SDS-PAGE), the protein was transferred to a PVDF membrane. After the membrane was treated with a blocking buffer (5% non-fat milk) for 1 hour in order to block non-specific binding of antibodies, the membrane was washed with a PBST solution containing 0.1% Tween 20. The membrane was treated at 4° C. overnight by using each antibody of a protein to be observed, HRP-linked anti-rabbit or anti-mouse was used as a secondary antibody, and the secondary antibody was color-developed by using ECL chemiluminescence detection reagents, and then observed by using an image analyzing system.

1-6. Experimental Animals

As experimental animals, female B6C3F1 mice with a body weight of 11 to 18 g were purchased from Central Lab. Animal Inc., acclimated to a laboratory environment while being supplied with sufficient feed and water for 1 week, and then used in the experiment. For the laboratory environment, a condition in which day and night continued in a unit of 12 hours was maintained until the end of the experiment while keeping the temperature at 22±2° C.

1-7. Preparation of Feed

By assuming that the amount of feed ingested by one mouse per day is 5 g, the intake concentration of the *Evodia rutaecarpa* Bentham extract was set to 100 mg/kg/day or 300 mg/kg/day and the extract was mixed with the feed to prepare an experimental meal (Feedlab Co., Ltd., Korea).

1-8. Induction of Premature Ovarian Failure

After VCD was dissolved in sesame oil (Sigma, USA), premature ovarian failure was caused by intraperitoneal injection at a concentration of 160 mg/kg/day once a day for 15 days, and the same amount of sesame oil was intraperitoneally injected into the normal group.

1-9. Selection of Experimental Group

Sesame oil was intraperitoneally injected into the normal group (control group), and sesame oil in which VCD was dissolved at a concentration of 160 mg/kg/day was intraperitoneally injected into the control (VCD group) and the experimental group (EF group). The normal group and the control were fed on a normal diet for 4 weeks, and the experimental group was fed on an experimental diet containing an *Evodia rutaecarpa* Bentham extract at a concentration of 100 mg/kg or 300 mg/kg for 4 weeks from a week prior to the VCD treatment.

1-10. Measurement of Body Weight and Uterine and Ovarian Weights

Based on the body weight measured on the initiation day of the experiment (day 1), the changes in body weight were observed every week. After the mice were sacrificed on the final day of the experiment, the weights were measured by removing the entire uterus and ovaries, only one ovary was separately cut off, the weight of the ovary was measured, and the result was processed as a ratio of the weight to the body weight immediately before the sacrifice.

1-11. Histopathological Observation

The one ovary and the uterus were fixed in 10% formalin and embedded in paraffin, 5 μm thin sections were made and stained with Hematoxylin-Eosin (H&E), and a general histopathological finding was observed and analyzed under an optical microscope.

1-12. Measurement of Blood AMH Content

On the final day of the experiment, blood was obtained from the mice by a cardiac blood collection method, and centrifuged at 3,000 rpm for 15 minutes by using a centrifuge (Beckman Coulter, Fullerton, Calif.) to take the supernatant. The AMH content in the obtained serum was measured by using a mouse AMH (Anti-Mullerian Hormone) ELISA kit (Elabscience).

Example 2. Confirmation of Antioxidant Efficacy of *Evodia rutaecarpa* Bentham Extract The antioxidant efficacies of the *Evodia rutaecarpa* Bentham, Cuscutae Semen, Artemisiae Argyi Folium, Dioscoreae Rhizoma, Aucklandiae Radix, and Ulmi cortex extracts prepared through Example 1-1 were measured and compared with one another.

Figure 2:
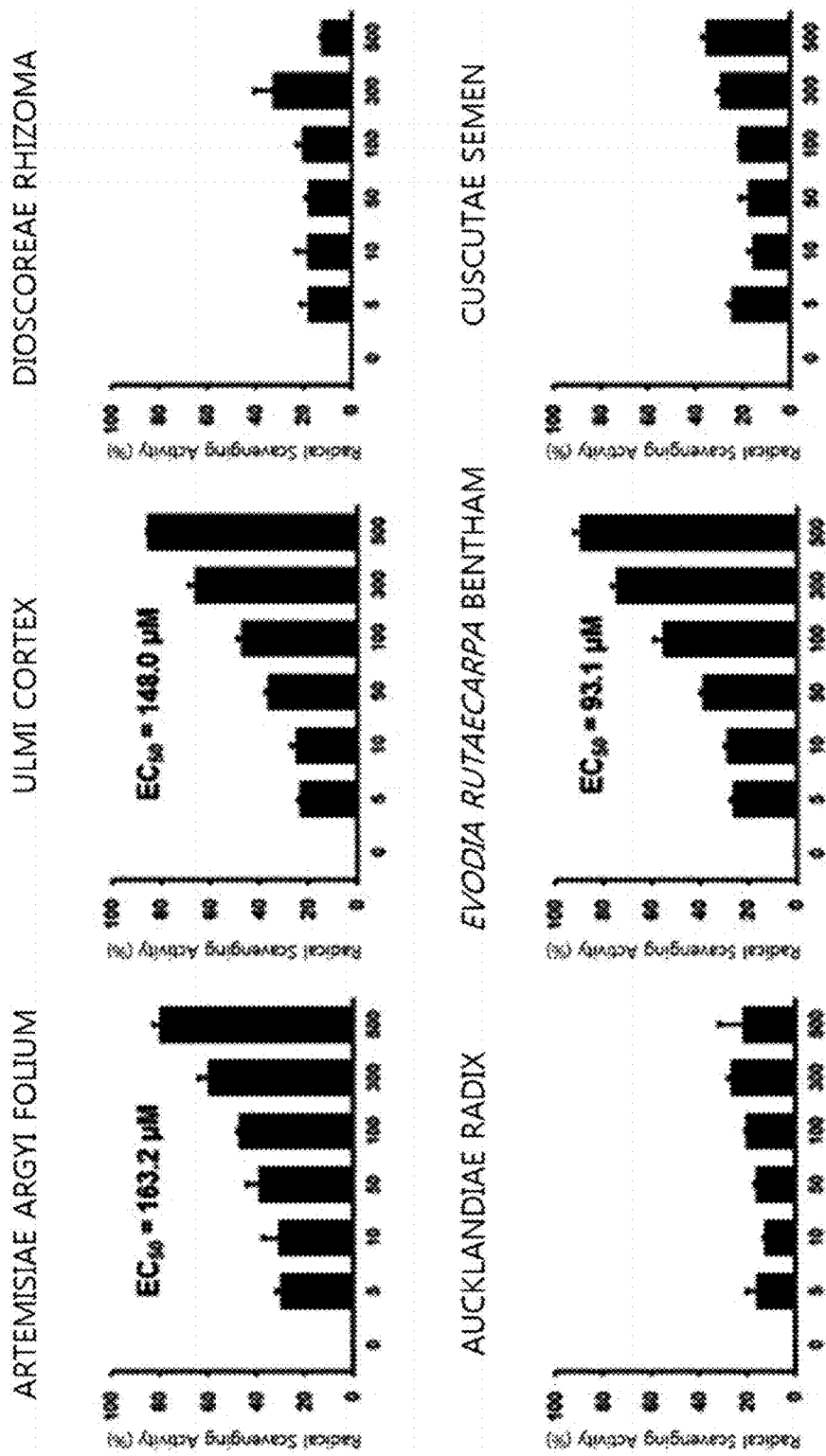
FIG. 2 is a result of comparing the DPPH radical scavenging activities of the *Evodia rutaecarpa* Bentham extract and extracts of 5 medicines (Cuscutae Semen, Artemisiae Argyi Folium, Dioscoreae Rhizoma, Aucklandiae Radix, and Ulmi cortex).

First, the DPPH radical scavenging activity of each extract was measured by the method described in Example 1-2, and as a result, as illustrated in FIG. 2, when the $EC_{50}$ (effective concentration 50%) of each of the 6 medicine extracts was confirmed, the $EC_{50}$ value of the *Evodia rutaecarpa* Bentham extract was 93.1 μM, which was shown to be the lowest value in the 6 medicines.

Figure 3:
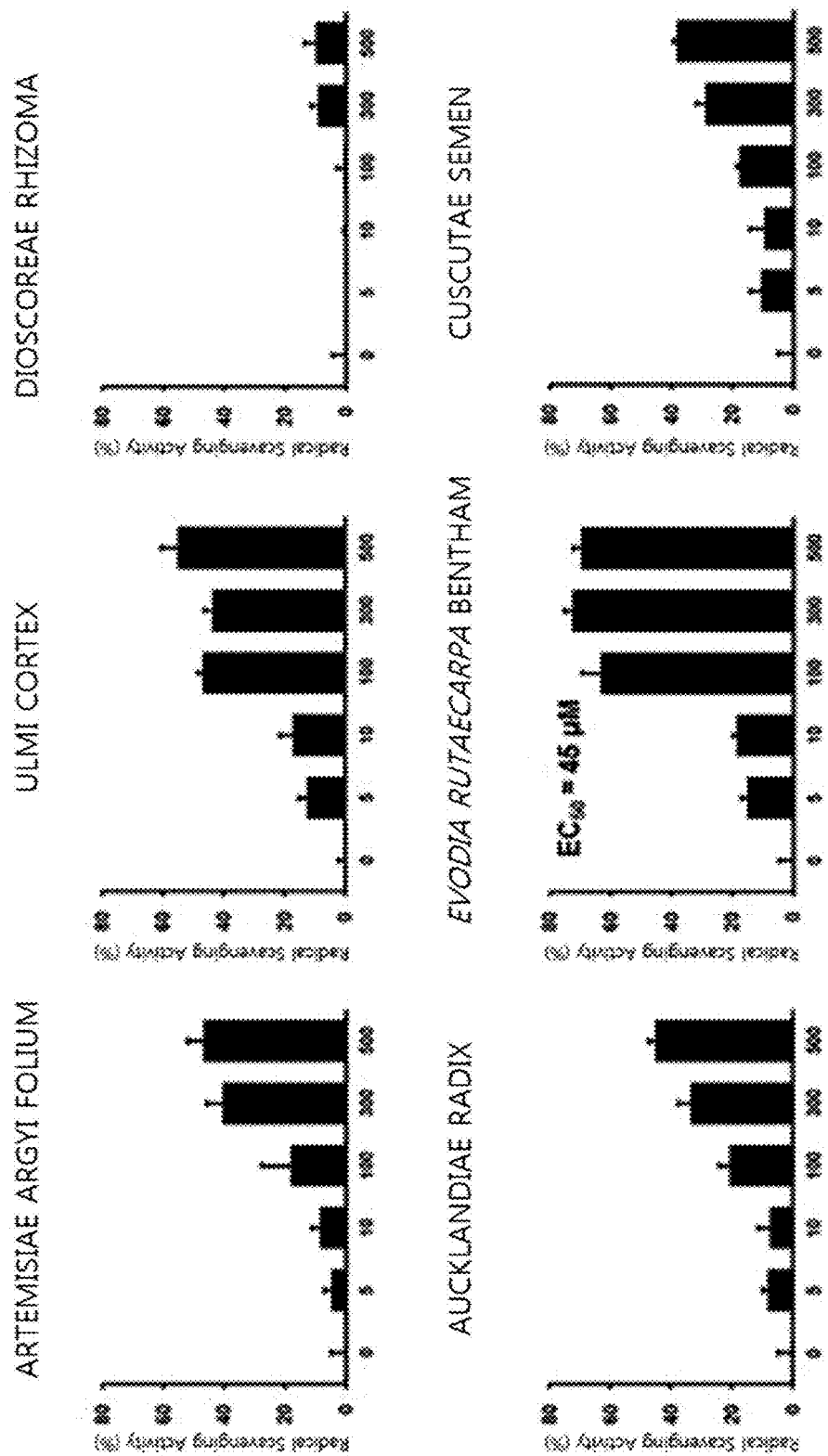
FIG. 3 is a result of comparing the superoxide anion scavenging activities of the *Evodia rutaecarpa* Bentham extract and extracts of 5 medicines (Cuscutae Semen, Artemisiae Argyi Folium, Dioscoreae Rhizoma, Aucklandiae Radix, and Ulmi cortex).

Next, the superoxide anion scavenging activity of each extract was measured by the method described in Example 1-3, and as a result, as illustrated in FIG. 3, it could be confirmed that the $EC_{50}$ of the *Evodia rutaecarpa* Bentham extract was the lowest similarly to the DPPH radical scavenging activity result.

Example 3. Confirmation of VCD Toxicity Against CHO-K1 Cells

Figure 4:
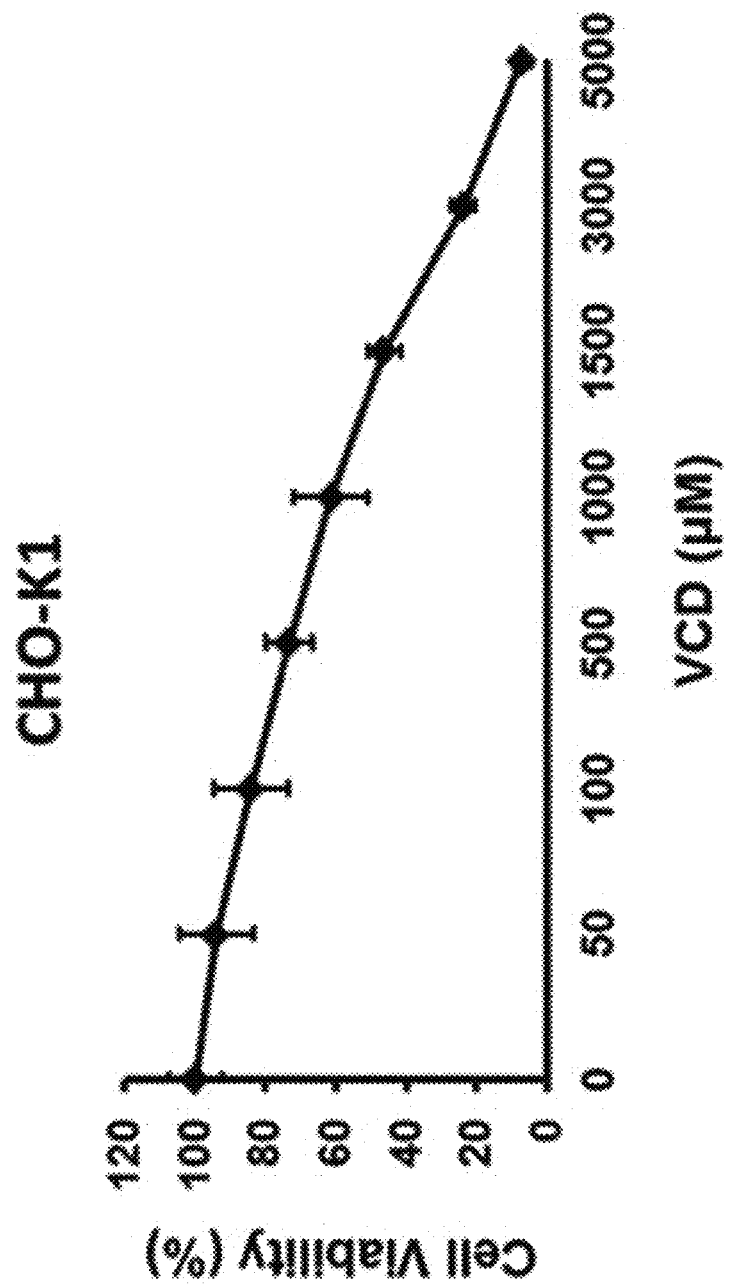
FIG. 4 is a result of confirming the cytotoxicity of VCD against CHO-K1 cells.

The cytotoxicity of VCD against CHO-K1 cells was evaluated by the MTT assay according to Example 1-4, and as a result, the concentration (1.5 mM) at which the viability of CHO-K1 cells by VCD became about 50% was determined (see FIG. 4), and the result was applied to the following experiment.

Figure 5:
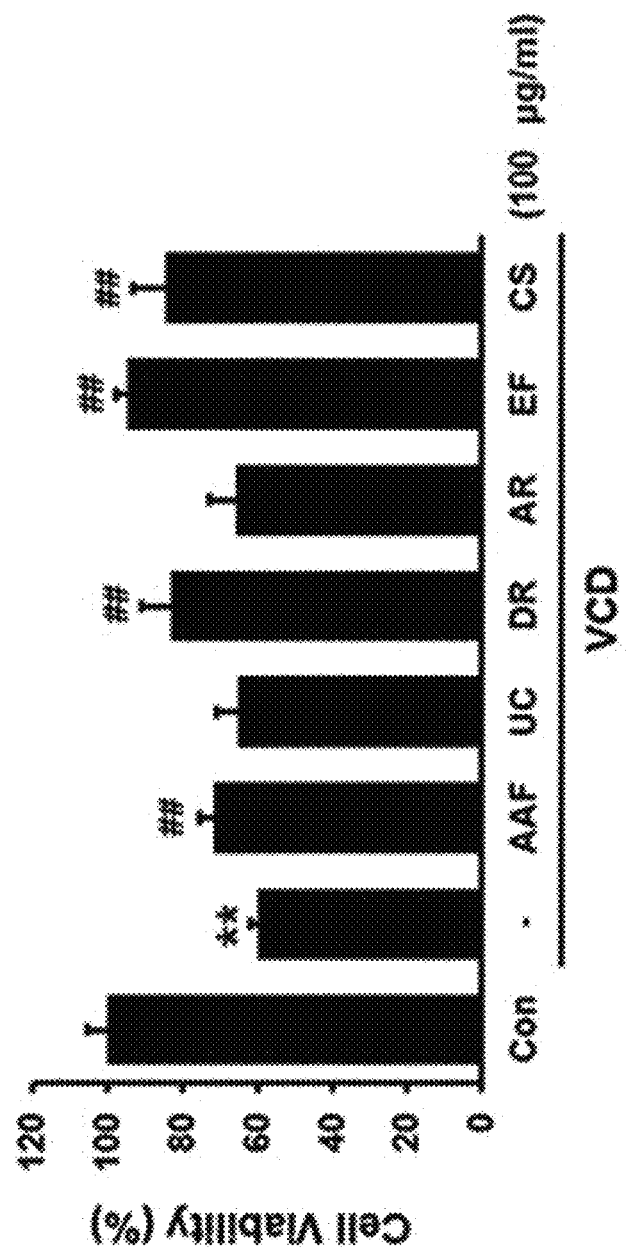
FIG. 5 is a result of confirming a protective effect of the *Evodia rutaecarpa* Bentham extract against ovotoxicity caused by VCD.

Example 4. Confirmation of Protective Effect of *Evodia rutaecarpa* Bentham Extract Against Ovotoxicity Caused by VCD For 2 hours before the treatment of CHO-K1 cells with 1.5 mM VCD, each of the *Evodia rutaecarpa* Bentham, Cuscutae Semen, Artemisiae Argyi Folium, Dioscoreae Rhizoma, Aucklandiae Radix, and Ulmi cortex extracts prepared through Example 1-1 was pre-treated at a concentration of 100 μg/ml, and then a screening of evaluating the protective efficacies of the extracts from the ovotoxicity caused by VCD was performed. As a result, as illustrated in FIG. 5, it could be confirmed that the *Evodia rutaecarpa* Bentham extract had the best protective efficacy from VCD as compared to the other 5 extracts.

Figure 6:
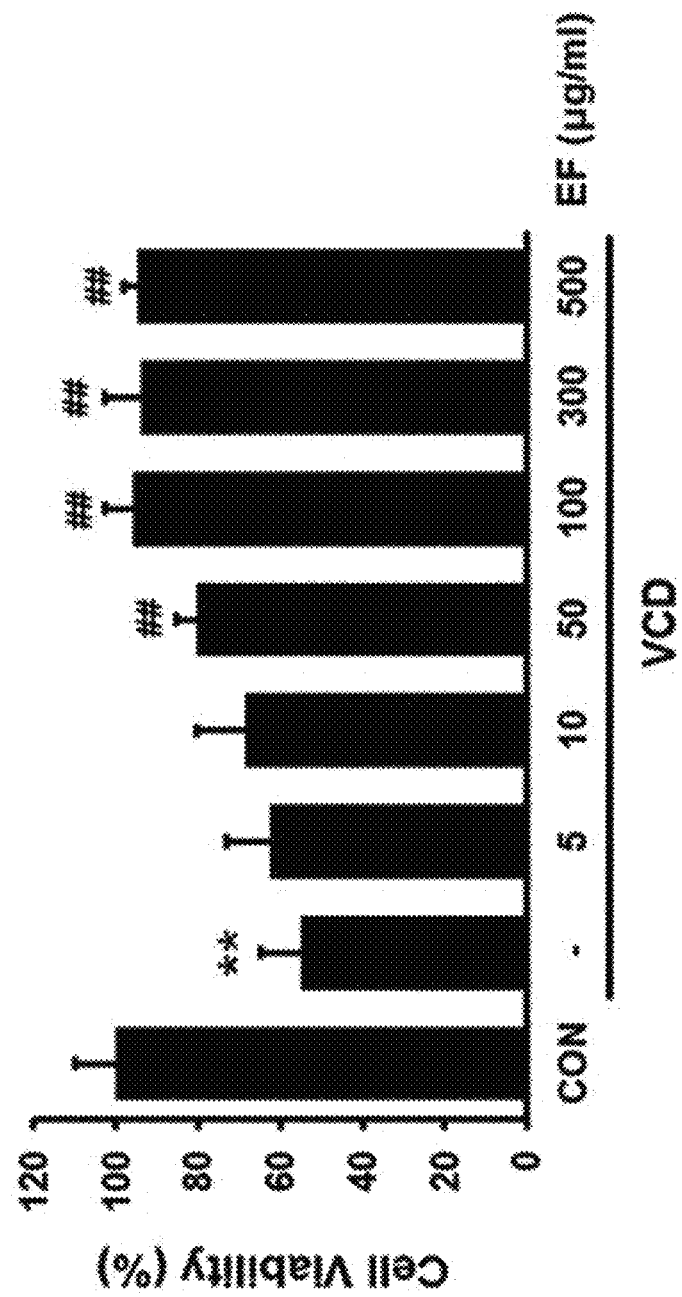
FIG. 6 is a result of confirming a protective effect of the *Evodia rutaecarpa* Bentham extract at each concentration against ovotoxicity caused by VCD.

Example 5. Confirmation of Protective Effect of
*Evodia rutaecarpa* Bentham Extract at Each
Concentration Against Ovotoxicity Caused by VCD CHO-K1 cells were pre-treated with the *Evodia rutaecarpa* Bentham extract at various concentrations (5, 10, 50, 100, 300, and 500 μg/ml) for 2 hours, ovotoxicity was caused by 1.5 mM VCD, and then the protective effect against the ovotoxicity was confirmed. As a result, as illustrated in FIG. 6, it could be confirmed that the *Evodia rutaecarpa* Bentham extract concentration-dependently exhibited a protective efficacy against ovotoxicity, and exhibited a viability almost similar to that of the control which had not been treated with VCD at a concentration of 100 μg/ml or more.

Figure 7:
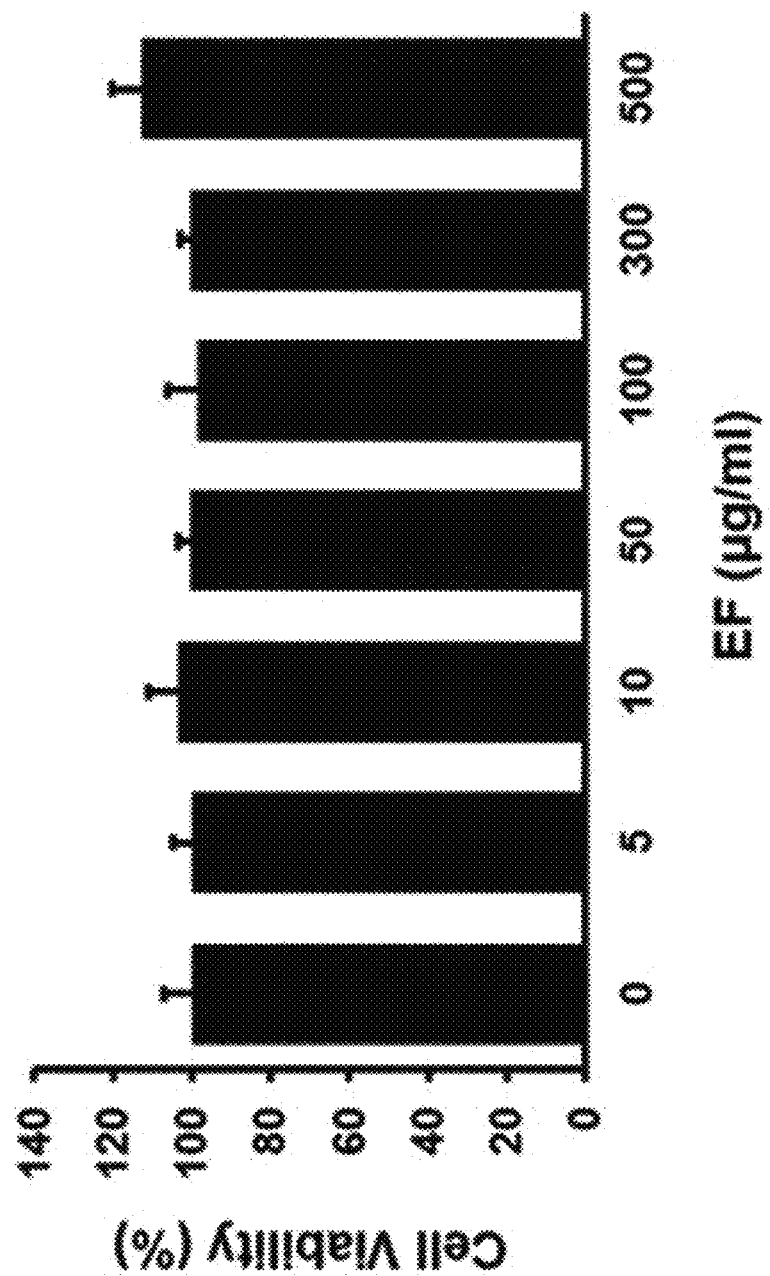
FIG. 7 is a result of confirming the cytotoxicity of the *Evodia rutaecarpa* Bentham extract alone against CHO-K1 cells.

Example 6. Measurement of Cytotoxicity of *Evodia rutaecarpa* Bentham Extract Alone Against CHO-K1 Cells After CHO-K1 cells were treated with the *Evodia rutaecarpa* Bentham extract alone at each concentration, the cytotoxicity of the *Evodia rutaecarpa* Bentham extract itself was evaluated through the MTT assay according to Example 1-4. As a result, as illustrated in FIG. 7, it was confirmed that when compared to the viability of the control, the viability of CHO-K1 cells was not affected until the concentration of 500 μg/ml.

Example 7. Confirmation of Effects of Inhibiting
Apoptosis Caused by VCD According to Treatment
with *Evodia rutaecarpa* Bentham Extract In order to confirm whether the apoptosis occurred, and the apoptosis caused by VCD was inhibited by the pre-treatment with the *Evodia rutaecarpa* Bentham extract (100 μg/ml) when CHO-K1 cells were treated with 1.5 mM VCD, the changes in expression of apoptosis-related protein (PARP, caspase-3) according to the treatment with the *Evodia rutaecarpa* Bentham extract were confirmed through the Western blot according to Example 1-5.

Figure 8:
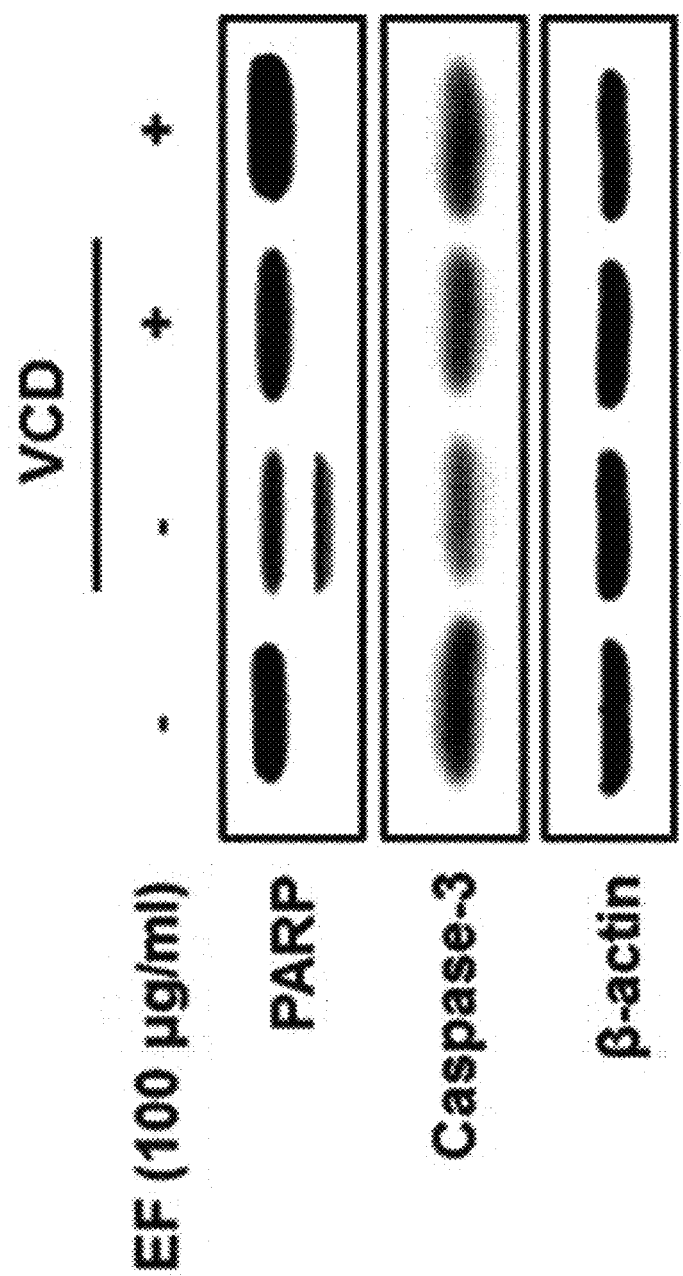
FIG. 8 illustrates effects of the *Evodia rutaecarpa* Bentham extract on apoptosis of CHO-K1 cells, which is caused by VCD.

As a result, as illustrated in FIG. 8, it could be confirmed that when compared to the control, in the case of the treatment with VCD, the PARP cleavage occurred and two bands appeared, and in the case of caspase-3 of the preform, the band intensity was decreased and the apoptosis was caused. In contrast, it could be confirmed that in the case of the pre-treatment with the *Evodia rutaecarpa* Bentham extract and the treatment with VCD, the PARP band was not separated into two, and even in the case of caspase-3, the band intensity was not decreased as compared to the treatment with VCD alone. From the results, it could be seen that the *Evodia rutaecarpa* Bentham extract had a cell protective effect from apoptosis caused by VCD, that is, ovotoxicity.

Example 8. Confirmation of Mechanism of
Protective Efficacy of *Evodia rutaecarpa* Bentham
Extract Against Ovotoxicity In order to examine the mechanism of the protective efficacy of the *Evodia rutaecarpa* Bentham extract against ovotoxicity, a change in PI3K/Akt signaling pathway, which is known to be a toxicity mechanism of VCD according to the treatment with the *Evodia rutaecarpa* Bentham extract, was confirmed through the Western blot according to Example 1-5.

Figure 9:
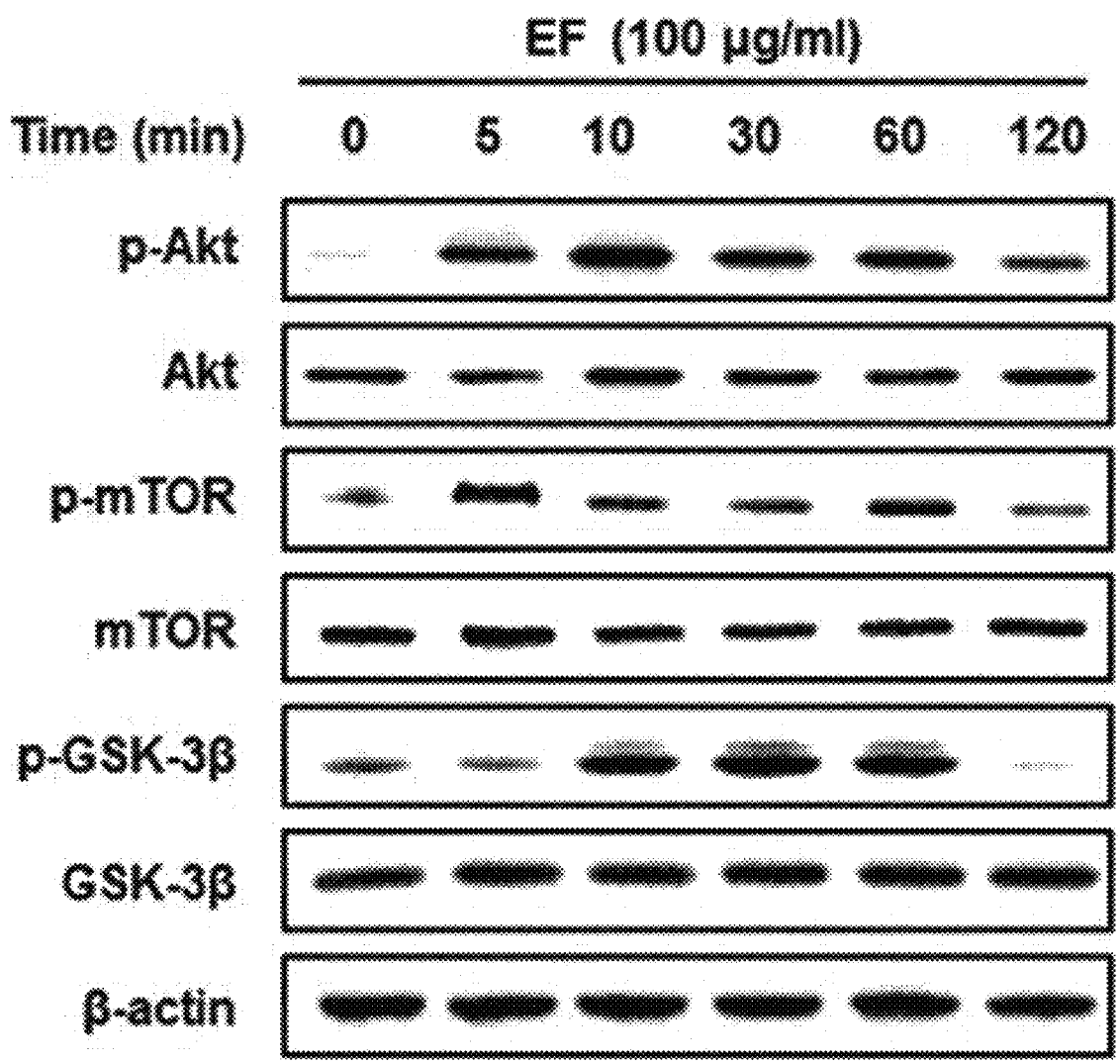
FIGS. 9 and 10 are results of confirming the changes in PI3K/Akt signaling pathway activity according to the treatment of the *Evodia rutaecarpa* Bentham extract.
Figure 10:
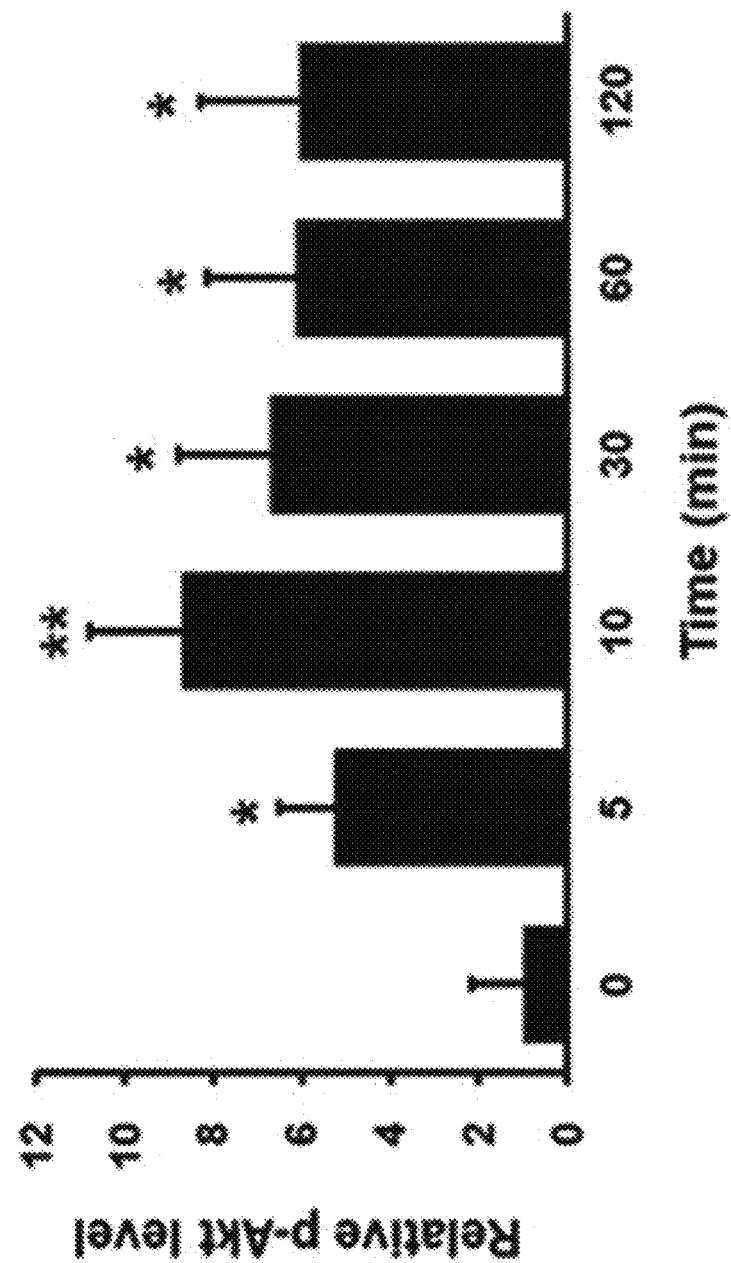

As a result, as illustrated in FIGS. 9 and 10, it was confirmed that the expression of Akt, mTOR, and GSK-3β, which are main kinases of the PI3K/Akt signaling was time-dependently activated toward the sub-signal treated with the *Evodia rutaecarpa* Bentham extract (100 μg/ml). That is, it could be confirmed that the PI3K/Akt signaling pathway was sequentially activated as a whole by the treatment with the *Evodia rutaecarpa* Bentham extract. From the result, it could be seen that the *Evodia rutaecarpa* Bentham extract had a cell protective efficacy from VCD through the activation of the PI3K/Akt signaling pathway.

Figure 11:
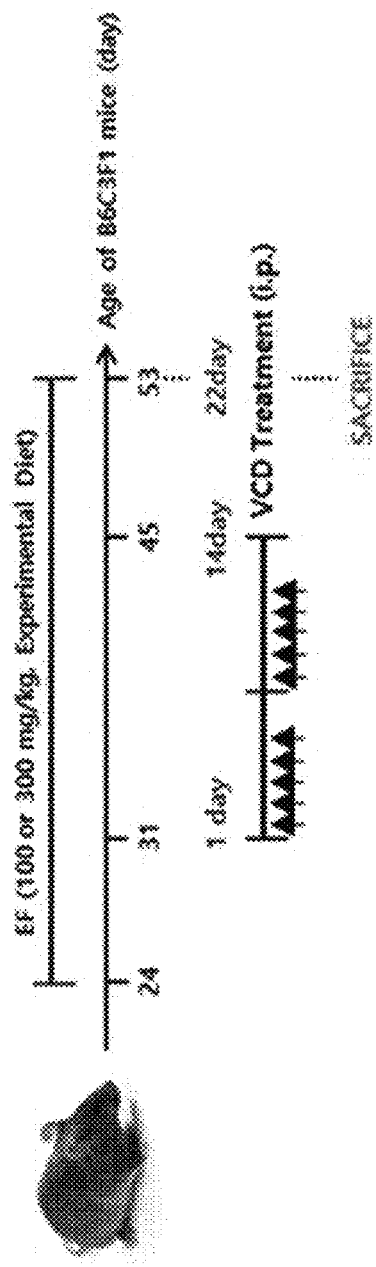
FIG. 11 is an animal experiment schematic view for evaluating an effect of the *Evodia rutaecarpa* Bentham extract on prevention of ovotoxicity.

Example 9. Confirmation of Preventive Effects of
*Evodia rutaecarpa* Bentham Extract Against
Premature Ovarian Failure Using In Vivo Animal
Model Based on the results of the Examples, the preventive effects of the *Evodia rutaecarpa* Bentham extract against premature ovarian failure were confirmed by using an animal model by the methods in Examples 1-6 to 1-12, and a schematic view of the experiment is illustrated in FIG. 11.

9-1. Macroscopic Observation of Uterine and Ovarian Tissues

Figure 12:
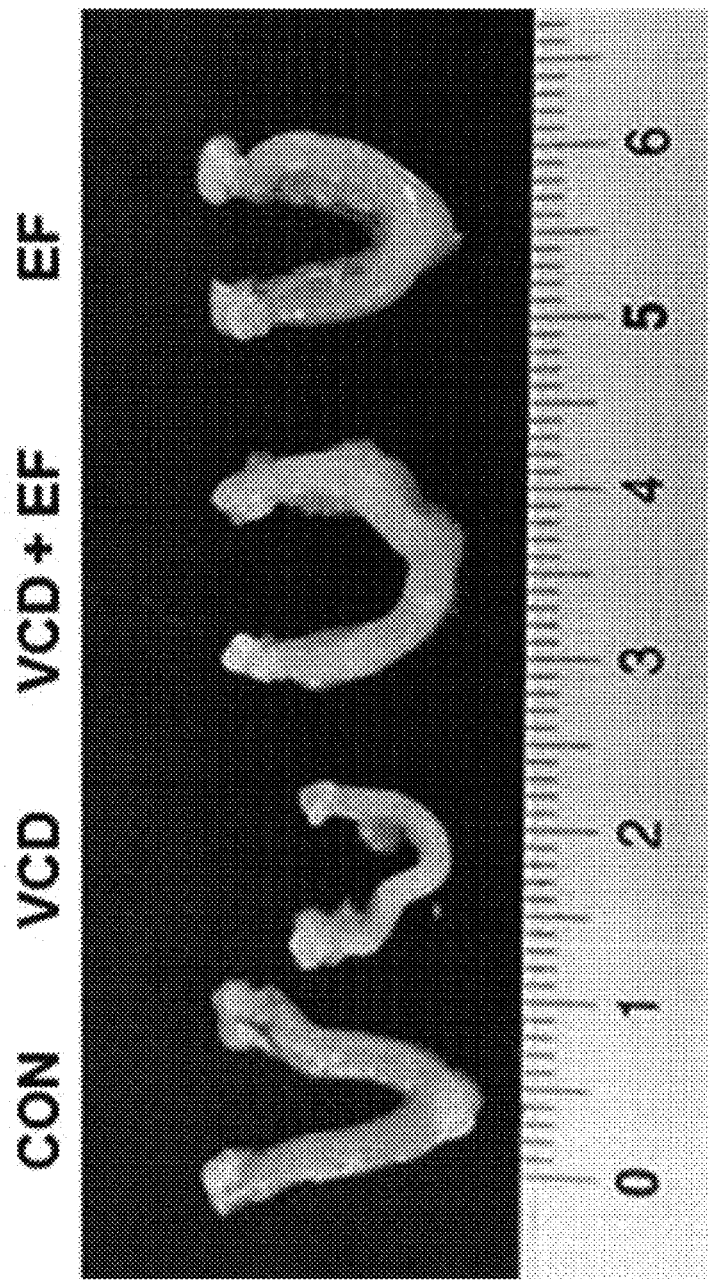
FIG. 12 is a macroscopic observation result of uterine and ovarian tissues according to the treatment of a control (CON), VCD, VCD+*Evodia rutaecarpa* Bentham (EF), and *Evodia rutaecarpa* Bentham (EF).

As a result of observing the uterine and ovarian tissues by the unaided eye, as illustrated in FIG. 12, it could be observed that the normal group maintained normal sizes in both ovarian and uterine tissues, whereas the VCD group was remarkably shrunk. Further, in the group to which VCD and *Evodia rutaecarpa* Bentham were administered, a size similar to that of the normal group was observed, and a specific macroscopic finding was not found similarly to the group to which *Evodia rutaecarpa* Bentham was administered alone.

Figure 13:
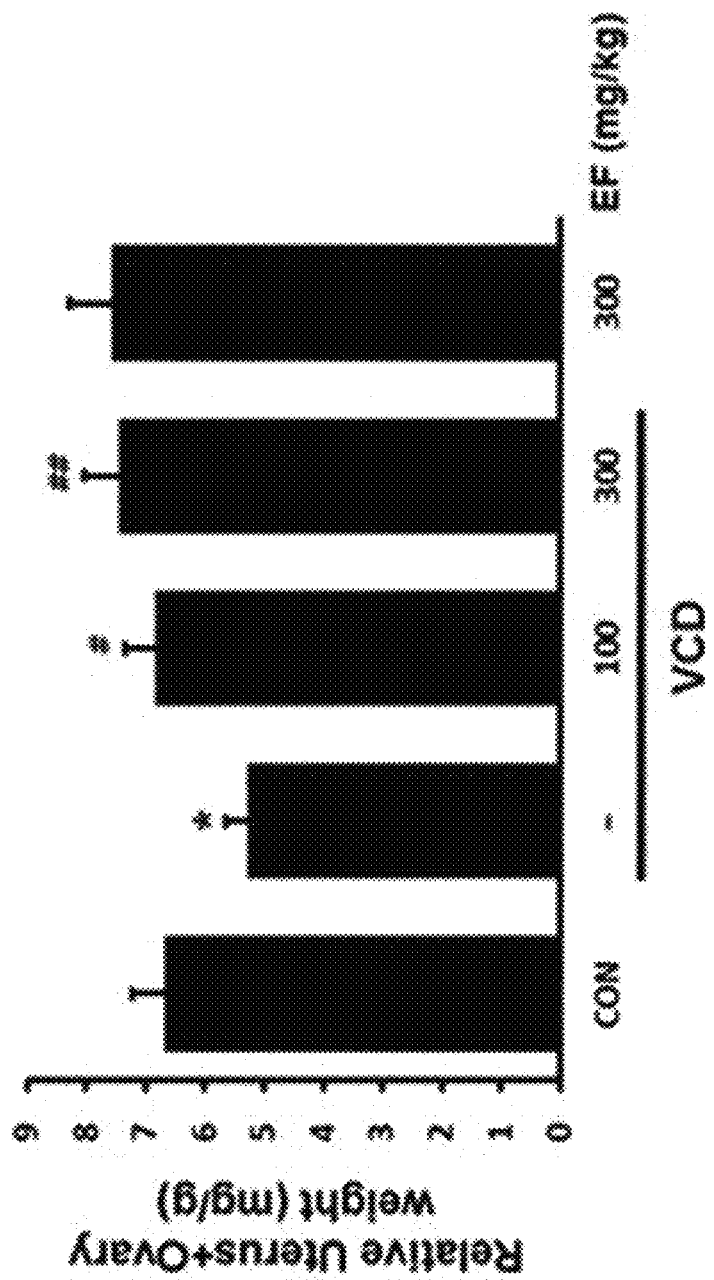
FIG. 13 is a graph illustrating weight indices of uterus and ovaries according to the treatment with an *Evodia rutaecarpa* Bentham extract.
Figure 14:
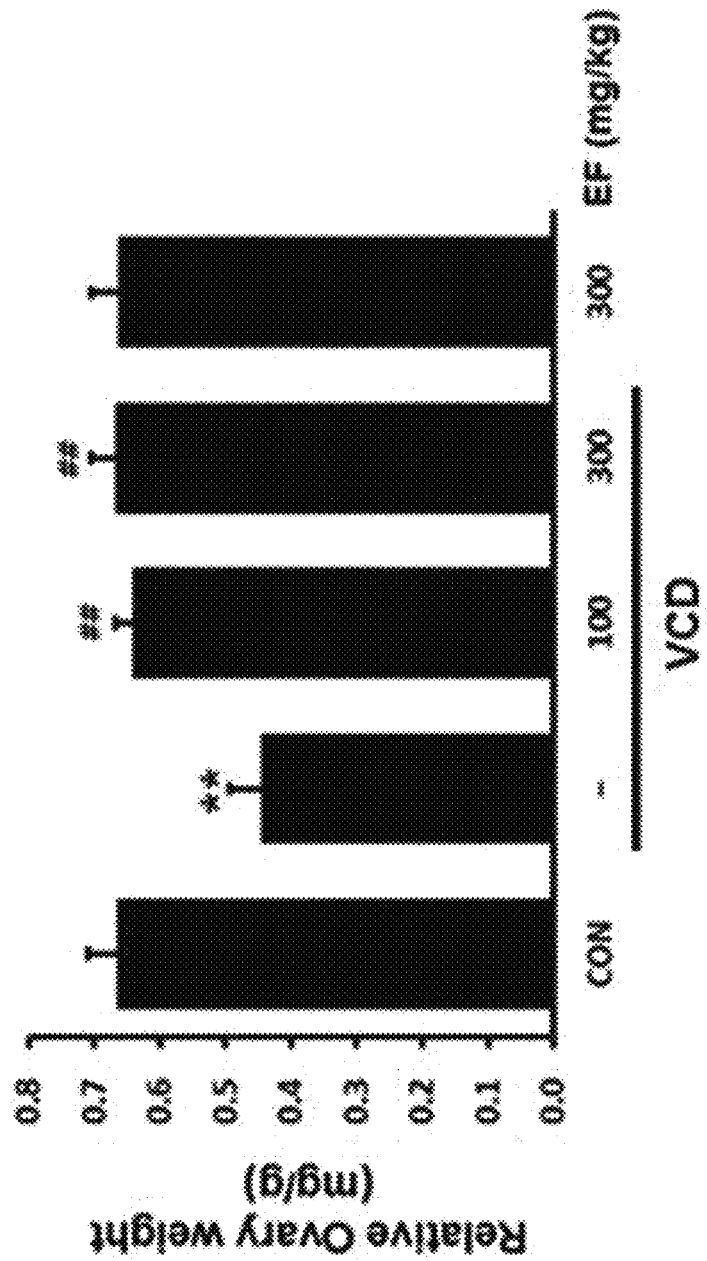
FIG. 14 is a graph illustrating weight indices of the ovaries according to the treatment with an *Evodia rutaecarpa* Bentham extract.

9-2. Confirmation of Ovarian/Uterine Protective Effects Through Comparison of Entire Weight of Uterus and Ovaries with Ovarian Weight As a result of comparing the entire weight of the uterus and the ovaries with the ovarian weight, as illustrated in FIGS. 13 and 14, it could be seen that the weights of the VCD group were significantly decreased as compared to those of the normal group, and the weights of the group to which VCD and *Evodia rutaecarpa* Bentham were administered were significantly concentration-dependently increased as compared to those of the VCD group, and the weights of the administration group were also almost similar to those of the normal group. In contrast, it was confirmed that the weight was not affected in the group to which *Evodia rutaecarpa* Bentham was administered alone. From the result, it could be seen that the administration of *Evodia rutaecarpa* Bentham effectively protected the ovaries and the uterus from the decrease in weight of the ovaries and the uterus caused by VCD.

9-3. Confirmation of Protective Effects of Ovaries Through Measurement of Blood AMH Content The anti-Mullerian hormone (AMH) is a hormone selected only in the ovarian follicles of the ovaries, and is a direct evaluation index that reflects the ovarian reserve well.

Figure 15:
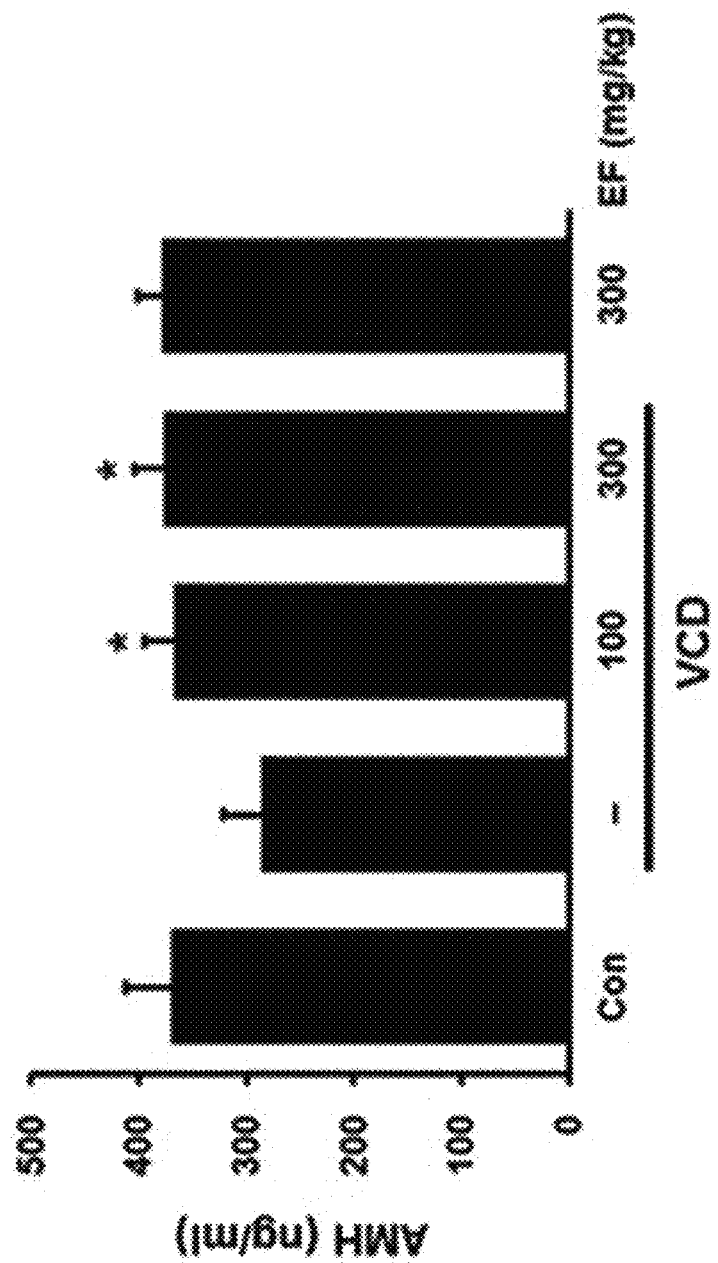
FIG. 15 is a result of measuring the concentrations of Serum anti-Mullerian hormone (AMH) secreted according to the treatment with an *Evodia rutaecarpa* Bentham extract.

Thus, as a result of measuring the blood AMH concentration by using an ELISA kit in the sera of the mice, as illustrated in FIG. 15, it could be confirmed that the VCD group did not exhibit a significance as compared to the normal group, but exhibited a tendency that the AMH concentration was decreased, and the AMH concentration in the group to which VCD and *Evodia rutaecarpa* Bentham were administered was similar to that of the normal group. Further, it could be seen that the group to which *Evodia*

*rutaecarpa* Bentham was administered alone did not affect the concentration of AMH. From the result, it could be seen that the administration of *Evodia rutaecarpa* Bentham had a protective effect of the ovaries from the decrease in AMH concentration caused by VCD.

Figure 16:
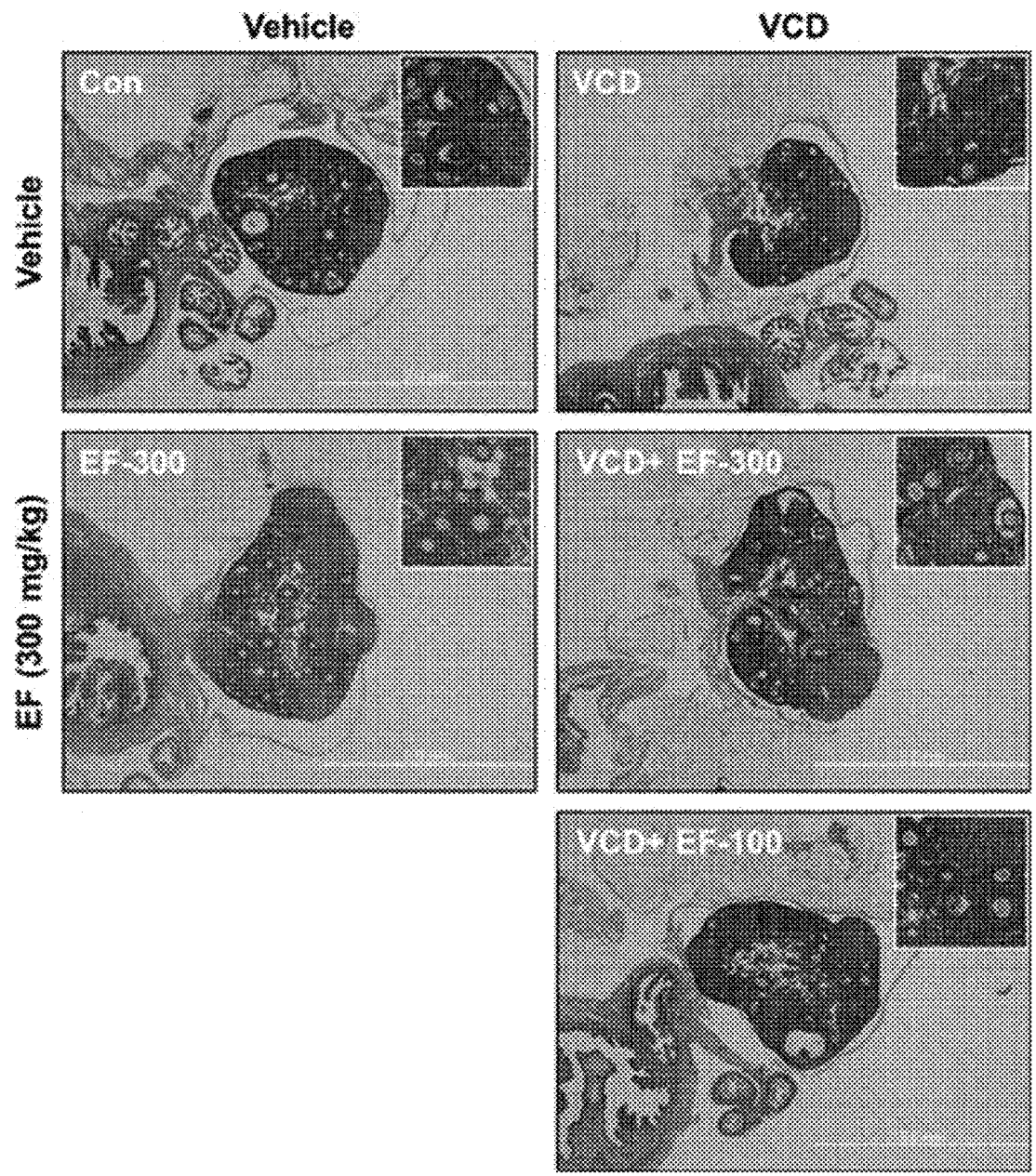
FIG. 16 is a histopathological analysis result of ovarian tissues through H&E staining.

9-4. Confirmation of Preventive Effect of Premature Ovarian Failure Through Histopathological Analysis As a result of the histopathological analysis through the H&E tissue staining, as illustrated in FIG. 16, the ovaries in the normal group maintained a normal size while mature ovarian follicles and corpora lutea were well developed in the primordial follicles with various sizes, but the ovaries in the VCD group exhibited a histological finding suggesting menopause, such as a remarkable decrease in sizes of the ovaries and a remarkable decrease in the number of ovarian follicles. In contrast, it could be confirmed that in the group to which VCD and *Evodia rutaecarpa* Bentham were administered, in the administration group at a high concentration of 300 mg/kg, the decrease in size of the ovaries or the degeneration in ovarian follicles and corpora lutea was not observed, and the administration group was almost similar to the normal group. From the result, it could be seen that the administration of *Evodia rutaecarpa* Bentham could prevent premature ovarian failure caused by VCD.

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

According to the present invention, the *Evodia rutaecarpa* Bentham extract concentration-dependently increases DPPH free radical scavenging activity so as to have excellent antioxidant activity, inhibits apoptosis of ovarian cells, and activates a PI3K/Akt signaling pathway so as to have a significant protective effect against ovotoxicity to be caused by 4-vinylcyclohexene diepoxide (VCD), thereby being usable as a medicine and a health functional food, which are useful for alleviating, preventing, inhibiting or treating ovotoxicity, premature ovarian failure and the like. Therefore, subfertility treatment or prevention, premature ovarian failure, a menopausal disorder in the premenopausal period, and the like can be considered application examples related thereto.

What is claimed is:

1. A method of treating ovotoxicity, the method comprising administering a therapeutically effective amount of an *Evodia rutaecarpa* Bentham extract to a subject in need thereof.

2. The method of claim 1, wherein the ovotoxicity is caused by 4-vinylcyclohexene diepoxide (VCD).

3. The method of claim 1, wherein the *Evodia rutaecarpa* Bentham extract inhibits apoptosis of ovarian cells.

4. The method of claim 1, wherein the *Evodia rutaecarpa* Bentham extract activates a PI3K/Akt signaling pathway.

* * * * *